(12) United States Patent
Ugochuku

(10) Patent No.: US 10,507,070 B2
(45) Date of Patent: Dec. 17, 2019

(54) SINGLE PORT MULTI-INSTRUMENT SURGICAL ROBOT

(71) Applicant: Ifeanyi Ugochuku, Redlands, CA (US)

(72) Inventor: Ifeanyi Ugochuku, Redlands, CA (US)

( * ) Notice: Subject to any disclaimer, the term of this patent is extended or adjusted under 35 U.S.C. 154(b) by 5 days.

(21) Appl. No.: 16/219,697

(22) Filed: Dec. 13, 2018

(65) Prior Publication Data

US 2019/0201132 A1 Jul. 4, 2019

Related U.S. Application Data

(60) Provisional application No. 62/611,444, filed on Dec. 28, 2017.

(51) Int. Cl.
| | |
|---|---|
| *A61B 34/30* | (2016.01) |
| *A61B 34/00* | (2016.01) |
| *A61B 90/50* | (2016.01) |
| *A61B 17/34* | (2006.01) |
| *A61B 17/29* | (2006.01) |
| *A61B 90/30* | (2016.01) |
| *A61B 17/00* | (2006.01) |

(52) U.S. Cl.
CPC .............. *A61B 34/30* (2016.02); *A61B 34/70* (2016.02); *A61B 17/3423* (2013.01); *A61B 90/30* (2016.02); *A61B 90/50* (2016.02); *A61B 2017/00362* (2013.01); *A61B 2017/2906* (2013.01); *A61B 2017/3466* (2013.01); *A61B 2034/301* (2016.02); *A61B 2034/302* (2016.02); *A61B 2090/506* (2016.02)

(58) Field of Classification Search
CPC ... A61B 34/30; A61B 34/70; A61B 2034/301; A61B 2034/302; A61B 17/3423; A61B 2017/3445; A61B 2017/3447
See application file for complete search history.

(56) References Cited

U.S. PATENT DOCUMENTS

| | | | |
|---|---|---|---|
| 9,179,979 B2 | 11/2015 | Jinno | |
| 2005/0096502 A1 | 5/2005 | Khalili | |
| 2011/0040305 A1* | 2/2011 | Gomez | B25J 9/1656 |
| | | | 606/130 |
| 2011/0118756 A1* | 5/2011 | Brock | A61B 34/71 |
| | | | 606/130 |
| 2011/0264136 A1 | 10/2011 | Choi et al. | |

(Continued)

*Primary Examiner* — Katherine M Rodjom
(74) *Attorney, Agent, or Firm* — Kenneth P. Avila

(57) ABSTRACT

Described herein is a surgical device configured for performing minimally invasive surgical procedures through a single incision via an introducer that allows one or more robotic main arm and two to four robotic secondary arms to be inserted into the insufflated surgical site. The main arm is capable of being inserted into and withdrawn from the insufflated surgical site autonomously, having the surgical tool at its distal end replaced autonomously, having five degrees of freedom, and having a diameter larger than that of a secondary arm. The secondary arms are capable of being inserted into and withdrawn from the insufflated surgical site autonomously and having four degrees of freedom. In the preferred embodiment the introducer is configured to allow one main arm and four secondary arms. In other embodiments the introducer allows for one or more main arms of varying diameters and one or more secondary arms of a smaller diameter.

8 Claims, 17 Drawing Sheets

(56) References Cited

U.S. PATENT DOCUMENTS

2011/0290855 A1\* 12/2011 Moore ................ A61B 17/072
  227/180.1
2014/0309659 A1  10/2014 Roh et al.
2017/0086927 A1\*  3/2017 Auld ...................... A61B 34/30
2017/0128143 A1   5/2017 Yeung et al.

\* cited by examiner

SINGLE PORT MULTI-INSTRUMENT SURGICAL ROBOT

CROSS-REFERENCE TO RELATED APPLICATIONS

This application claims priority from U.S. Provisional Patent Application No. 62/611,444 filed on Dec. 28, 2017. The entire disclosure of the prior application is considered to be part of the disclosure of the accompanying application and is hereby incorporated by reference.

BACKGROUND OF THE INVENTION

1. Field of the Invention

The present disclosure relates generally to surgical systems, devices, and methods, and more specifically, relates to a device for use in performing Minimally Invasive Surgery (MIS) procedures that allows for the deployment of multiple surgical tools to a surgical site through a single incision.

2. Description of the Related Art

MIS has increasingly become more desirable as this class of surgical procedures is performed through multiple small incisions on the patient's body to minimize tissue damage and blood loss during surgery and conducting the surgery through these small incisions by means of thin and rigid instruments that are passed through an introducer placed within the incisions to the surgical site. The success of various MIS procedures in decreasing patient pain and improving recovery time has driven the trend to develop devices and procedures that would allow less invasive surgical procedure to be performed.

Much of the success in MIS procedures have been driven by advances in the instruments used. At the start, MIS procedures were performed with the help of a small endoscopic camera in one incision and several long, thin, and rigid instruments projected to the surgical site through other incisions. Many times the surgical site is insufflated to give the surgeon more space with which to maneuver the instruments. As an example, in a typical laparoscopic cholecystectomy (gallbladder removal) procedure, a needle is inserted into the abdomen and the abdomen is insufflated by pumping $CO_2$ gas into the abdomen. Once the abdomen is inflated, an endoscopic camera is inserted into the abdomen through an introducer inserted within an incision around the navel region so that the surgeon may view the surgical site. Additional instruments are then inserted into the abdomen through introducers inserted into incisions made to the right and left side of the endoscope incision. The instruments have the appearance of a long and rigid rod with a surgical tool, such as a forceps or scissors, attached at the distal end of the rod and a handle with controls to manipulate the surgical tool attached at the proximal end of the instrument. The surgeon positions the surgical tool by gripping the handle to further insert or withdraw the instrument or to change the instrument's angular approach. Mechanical connections are provided within the rod so that the surgeon may operate the surgical tool at the distal end of the instrument through the controls present on the handle. Returning to the example, the surgeon may insert needed instruments through the incisions, withdraw instruments that are no longer needed to be replaced with other instruments to dissect out the gallbladder from its surrounding tissues, seal off blood vessels, and remove the gallbladder from the abdomen.

In spite of the advantages brought by MIS procedures such as decreasing patient pain and improve recovery time, the technique does introduce certain disadvantages for the surgeon. A first disadvantage is since the instruments are long and rigid, only with great difficulty and patience may incisions support more than one instrument passing therethrough. As a result additional incisions are required causing more pain and trauma to the patient and increasing the patient's recovery time. A second disadvantage is the difficulty of properly manipulating the rather unwieldy long and rigid instruments through the "eye" of the laparoscope and creating hand-eye coordination problem with the surgeon. This problem is exacerbated in longer surgeries as fatigue sets in on the surgeon's arms.

To avoid these disadvantages and others, surgeons have begun to replace the hand manipulated instruments with first generation MIS systems based on a set of robotic arms that are manipulated by a computer that is under the control of a surgeon via a Human Machine Interface (HMI). HMI is a component of a system that is capable of handling the interaction between a human and a machine. The interface consists of hardware and software that allow user inputs to be translated as signals for machines that, in turn, provide the required result to the user. Thus the surgeon may perform the surgery remotely from the patient at a console using hand and finger gestures that are translated into signals that control the robotic arms holding the instruments and the surgical tools found at the distal end of the instrument. This alleviates problems with a surgeon's hand-eye coordination as the HMI may compensate for spatial differences between the surgeon's hand and finger gestures and the position and actions of the surgical tool at the end of the instruments as well as reduce the amount of fatigue experienced by the surgeon during longer or more demanding surgeries.

Newer second generation MIS systems have focused on a number of improvement over first generation systems. These improvements includes, among others, increasing the number of instruments that may be inserted through a single incision, automating the removal of instruments from the abdominal cavity, and automating the process of replacing the surgical tool attached to the distal end of an instrument. The surgical device of the present disclosure is of a design so as to maximize the number of instruments that may be introduced into the abdominal cavity through a single incision, automates the removal of these instruments from the abdominal cavity, and allows for the automated replacement of a surgical tool at the distal end of at least one instrument.

An example of a second generation MIS system is found in US patent publication 2005/0096502 to Theodore Kahlili. The Kahlili disclosure shows a robotic surgical device configured for performing MIS procedures where there is only a single incision. The robotic surgical device comprises an elongated body for insertion into a patient's body through a small incision that houses a plurality of robotic arms that are deployed within the abdominal cavity for surgical purposes. An image detector may be positioned at the distal portion of the elongated body or on one of the robotic arms to provide visual feedback to the operator of the device. In another variation, each of the robotic arms comprises two or more joints, allowing the operator to maneuver the robotic arms in a coordinated manner within a region around the distal end of the device. However in the Kahlili disclosure only three robotic arms are able to be introduced into the abdominal cavity. As functionality, primarily degrees of freedom, are added to a robotic arm so the arm's diameter must increase to accommodate the added functionality. Given that it is desirable to make the incision as small as possible, each added functionality causes the arm to occupy a greater portion of the space provided by the incision; effectively limiting the number of robotic arms that may pass through the incision. Here, as all the robotic arms have similar functionality, their diameters are equal and only three are able to pass through the incision. In addition the arms of the Kahlili disclosure must be manually withdrawn from the abdominal cavity as shown in FIG. 5 where three separate robotic arms, 84, 86, and 88 are to be inserted into the abdominal cavity through deployment conduit 82 by the user manually pushing the robotic arms through the deployment conduit. Finally the surgical tool must be replaced manually as shown in FIG. 6 of the Kahlili disclosure where the distal end 102 of the individual robotic arm may have an interchange adaptor such that the surgeon may attach different surgical tools 104 to the robotic arm based on the particular need of the surgery to be performed.

Another example of a second generation MIS system is found in US patent publication 2014/0309659 to Se Gon Roh and others. Roh discloses a surgical device that includes a plurality of robotic arms to perform surgery at a surgical site within the abdominal cavity. The robotic arms include surgical position regulators to move the arms from the single port to a first surgical site. The single-port surgical robot may effectively perform simultaneous surgery upon various surgical regions like multi-port surgery. Roh does disclose a surgical device intended to introduce multiple robotic arms, four, into the abdominal cavity through a single incision. In the Roh disclosure only four robotic arms are able to be introduced into the abdominal cavity. As functionality, primarily degrees of freedom, are added to a robotic arm so the arm's diameter must increase to accommodate the added functionality. Given that it is desirable to make the incision as small as possible, each added functionality causes the arm to occupy a greater portion of the space provided by the incision; effectively limiting the number of robotic arms that may pass through the incision. Here, as all the robotic arms have similar functionality, their diameters are equal and only four are able to pass through the incision. Although the arms of the Roh device have a large number of degrees of freedom, once they have entered the abdominal cavity it is not possible to remove just a single arm to change the surgical tool at its distal end. All four arms enter as a group and must withdraw from the abdominal cavity as a group. It will not be possible to accomplish a MIS procedure that requires more than the four tools provided in the Roh disclosure and if different surgical sites require a different set of tools the entire device must be withdrawn from the abdominal cavity disrupting the surgery.

As discussed above, MIS procedures are preferred because the smaller incisions on the patient's body minimizes tissue damage and blood loss during surgery, decreases the amount of pain experienced by the patients, and reduces the amount of time required for recovery. As a result surgeons are seeking to improve MIS procedures so that only one incision, also referred to as a single port, is required and that multiple robotic arms may pass through the one incision further reducing tissue damage and blood loss during surgery. Prior art does disclose surgical devices with multiple robotic arms that pass through a single port. However the prior art does not disclose automated means of removing one of the multiple robotic arms nor automated means of changing the surgical tool at the distal end of a robotic arm. In addition the prior art gives each arm the same functionality requiring that each arm have similar complexity and a diameter proportional to the arm's functionality. It is important to keep the diameter of the robotic arms at a minimum in order to allow for a greater number of arms to pass through the incision yet providing the same functionality to all of the arms increases the cost of the surgical device as well as limiting the number of arms that may pass through the incision at the same time. The surgical device of the present disclosure seeks to address these problems.

BRIEF SUMMARY OF THE INVENTION

Described herein is a surgical device for deploying and utilizing multiple robotic arms of varying capabilities inside a patient through a single incision. Generally a single main arm will have certain capabilities; such as additional degrees of freedoms, power, and autonomous replacement of the attached surgical tool; not found on the remaining arms but such arm will have a greater diameter than the remaining and less capable arms. In the preferred embodiment, the device comprises one main arm and four secondary arms along with mechanisms to control the arms so that they may be raised, lowered, rotated, and otherwise manipulated by signals generated by a computer that is controlled by a surgeon. The arms are comprised of multiple cylindrical segments with the first segment proximate to the device being the longest and for the most part existing outside of the body. The remaining cylindrical segments are much shorter and are to operate within the patient's body. Finally, at the distal end of each arm, is a surgical tool such as but not limited to dissectors, cameras, lights, graspers, scissors (cautery or non-cautery capable), staplers, needle drivers, electrocautery hooks, retractors, clip appliers, cauterizer, or irrigation tubes. The surgical tool on the main arm may be autonomously replace by any one of a number of tools present on a carousel found on the surgical device while the surgical tool on any one of the secondary arms may be replaced by autonomously lifting the arm to expose the surgical tool so that it may be manually replaced by the surgeon.

In the prior art, each of the robotic arms are identical in terms of size, degrees of freedom, autonomous control, power consumption, and strength of the actuators and servos. However, it is understood that some surgical tools, such as cameras or lights, do not require as much autonomous control as other surgical tool such as dissectors or scissors. Thus when decreasing an arm's sophistication or strength, the arm's diameter may be minimized and a greater number of such arms, referred to as secondary arms, may fit through a single incision. Conversely, when increasing an arm's sophistication or strength, the arm's diameter will also increase and limit the number of such arms, referred to as main arms, that may fit through a single incision. It is advantageous to allow the surgeon to select the capabilities of the arms according to the needs of the procedure. In certain procedures a surgeon may find it beneficial to use many secondary arms and only one main arm. Other procedures would benefit from using multiple main arms and only a single secondary arm. As discussed above, the main arm of the surgical device of the present invention has additional capabilities not found in the secondary arms and as a result it will have a greater diameter than the diameter of the secondary arms. The main arm has more degrees of freedom, may house larger actuators and motors, and may autonomously replace the tool found at its distal end with another tool. The secondary arms are more restricted in their range of motion, lack the strength of the main arm, and require that the tool found at its distal end be replaced manually. The main arm, being of a larger diameter, may be used to remove body parts that have been dissected out of the patient's body.

Both the main and secondary arms may be raised, lowered, or rotated by mechanisms operating on the arms outside of the patient's body. Additionally, the main arm interfaces with a rotating carousel containing multiple grips with each grip capable of holding a surgical tool that is used by the main arm. When positioned to interface with the carousel, the surgical tool currently attached to the main arm may be replaced by a surgical tool found in the carousel. To change a tool attached to a secondary arm the surgeon will raise the secondary arm out of the patient's body and manually replace the tool with a desired tool. Replacing the surgical tool of the main or a secondary arm does not require that any of the remaining arms must also be withdrawn from the surgical site.

The surgical device is to be controlled by a computer system that will provide the appropriate power and signals to the various mechanisms in response to inputs received by the HMI from the surgeon. Any number of HMIs may be used to convert human gestures provided by the surgeon into signals that are sent by the computer system to the various mechanisms. The computer system and the associated man-machine interface are not part of this disclosure.

BRIEF DESCRIPTION OF DRAWINGS

The present invention will become more fully understood from detailed description and accompanying drawings, wherein.

DETAILED DESCRIPTION OF THE INVENTION

The following description of the preferred embodiment(s) is merely exemplary in nature and is in no way intended to limit the invention, its application, or uses.

Figure 1:
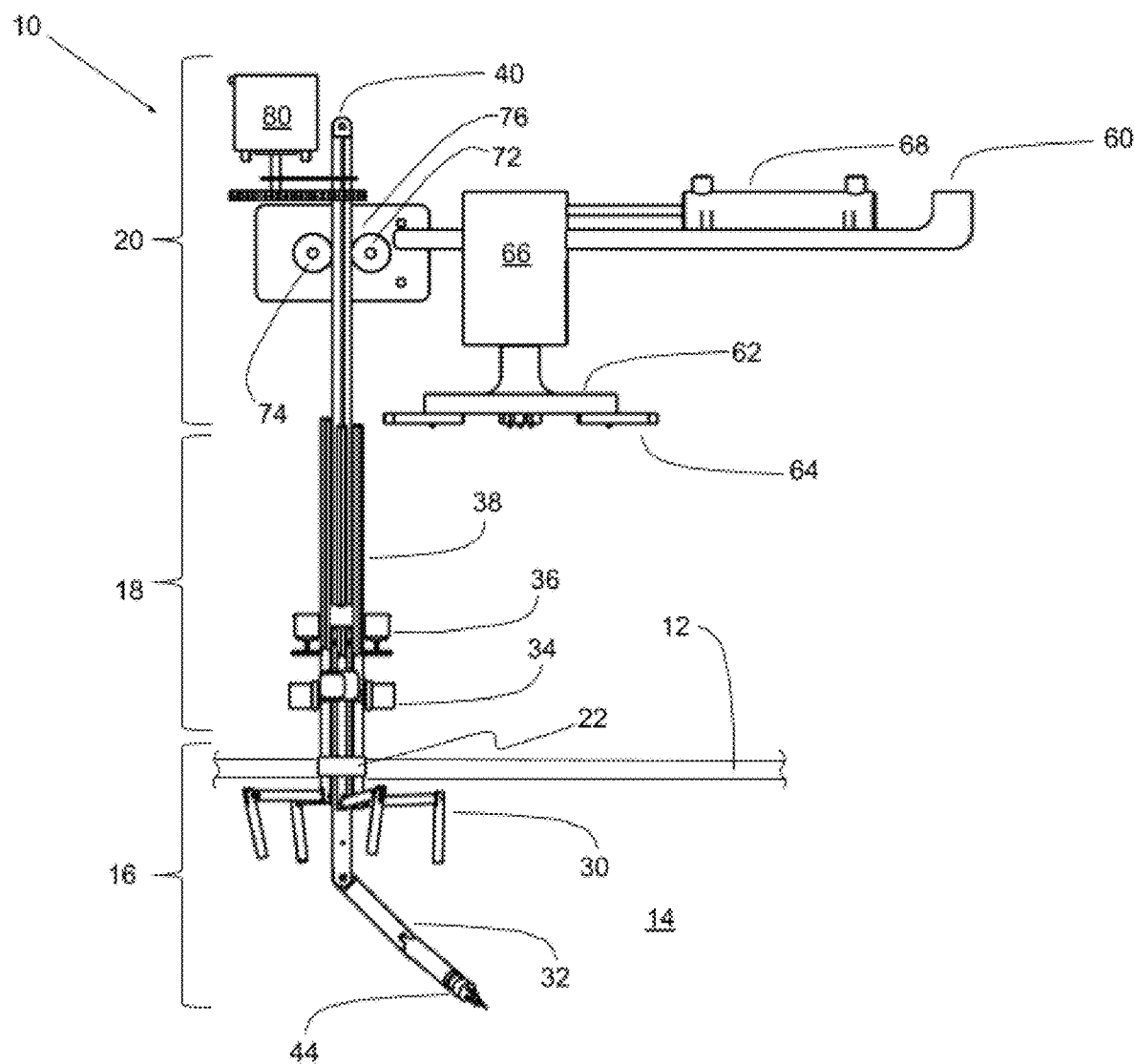
FIG. 1 shows a side view of the surgical device of the present invention.
Figure 2A:
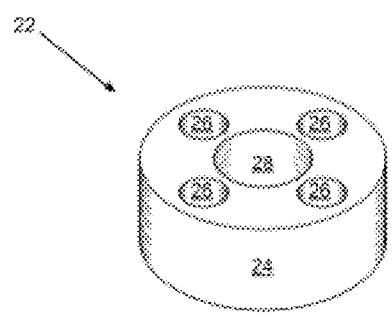
FIG. 2A shows an isometric vi of the preferred embodiment of the introducer containing a single larger opening for the main arm and four smaller openings for the secondary arms.

FIG. 1 shows a side view of the preferred embodiment of the surgical device 10 with its outer housing removed so as to reveal the members and mechanisms within the housing. In addition, FIG. 1 also shows abdominal wall 12 of the patient currently undergoing surgery with surgical device 10 lower portion 16 being within, for the most part, abdominal cavity 14. The housing of surgical device, which is not shown, encloses upper portion 20 and mid portion 18 and does not extend into abdominal cavity 14 so that secondary arms 30 as well as main arm 32 are free to maneuver within abdominal cavity 14. Secondary arms 30 are attached to cylindrical secondary shafts 38 and main arm 32 is attached to cylindrical main shaft 40. The proximal end of both main shaft 40 and secondary shaft 38 is the end furthest from abdominal cavity 14 with the distal end being that end closest to abdominal cavity 14. The proximal end of main arm 32 is the end attached to the distal end of main shaft 40 while the distal end of main arm 32 is the end holding the surgical tool ("tool"). The proximal end of secondary arms 30 is the end attached to the distal end of secondary shaft 38 while the distal end of secondary arms 30 is the end holding the tool. These shafts may be lifted from or lowered into abdominal cavity 14 as well as be rotated about their longitudinal axis independently from each other. In the preferred embodiment, all five shafts pass through introducer 22 as shown in FIG. 2A. Introducer 22 comprises disk 24 with five openings: four openings 26 for secondary arms 30 and one opening 28 for main arm 32. Secondary arm openings 26 are positioned about the edge of disk 24 and spaced about main arm opening 28. Alternative embodiments of introducer 22 are shown in FIG. 2B through FIG. 2E where the number of openings vary from the five found in the preferred embodiment of FIG. 2A.

Figure 3:
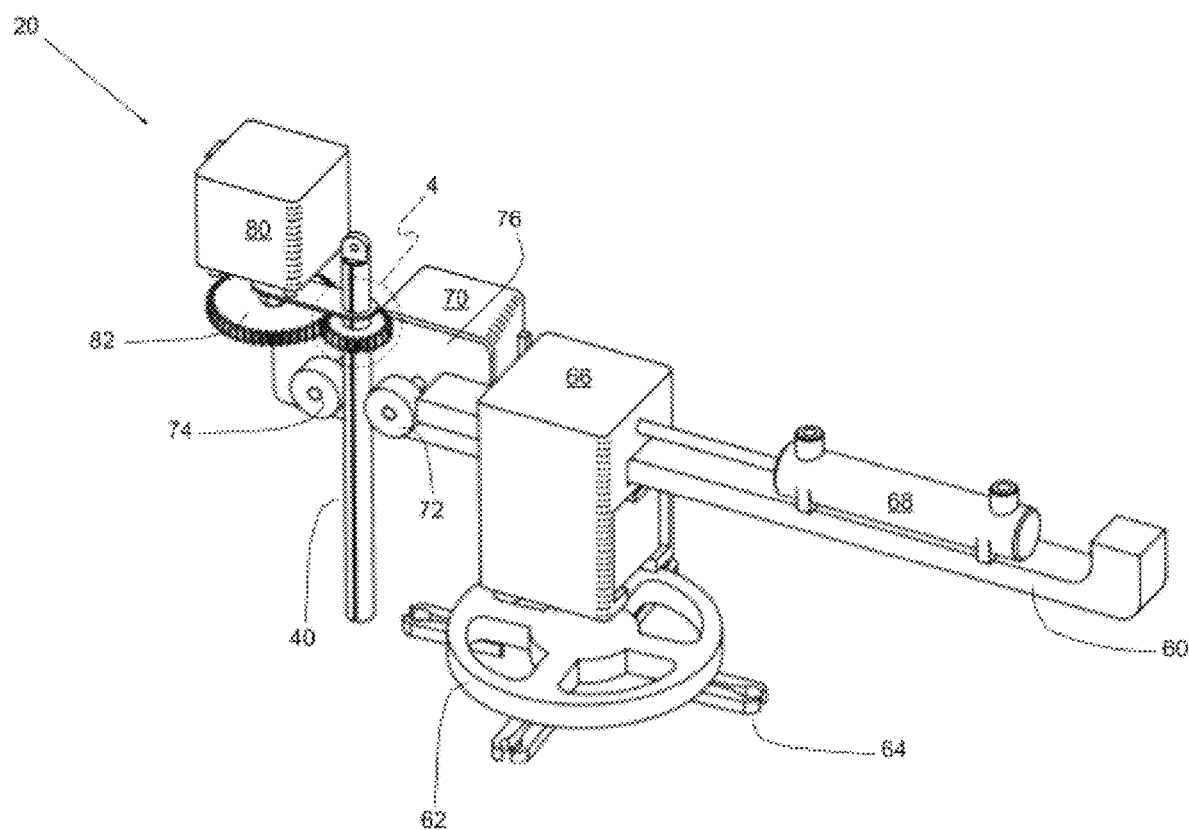
FIG. 3 shows an isometric view of the upper portion of the surgical device.
Figure 4:
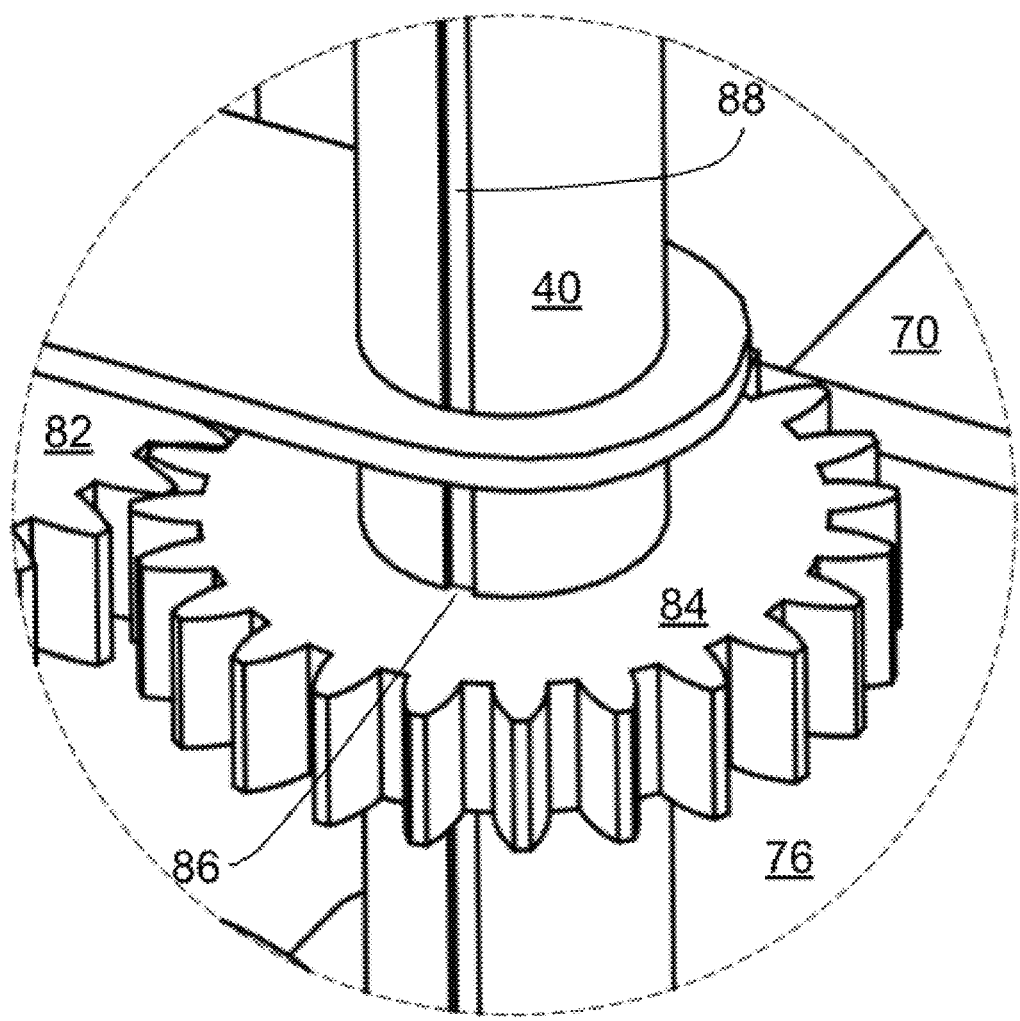
FIG. 4 shows a detail view of the key and keyway slot used to rotate the main arm.
Figure 7:
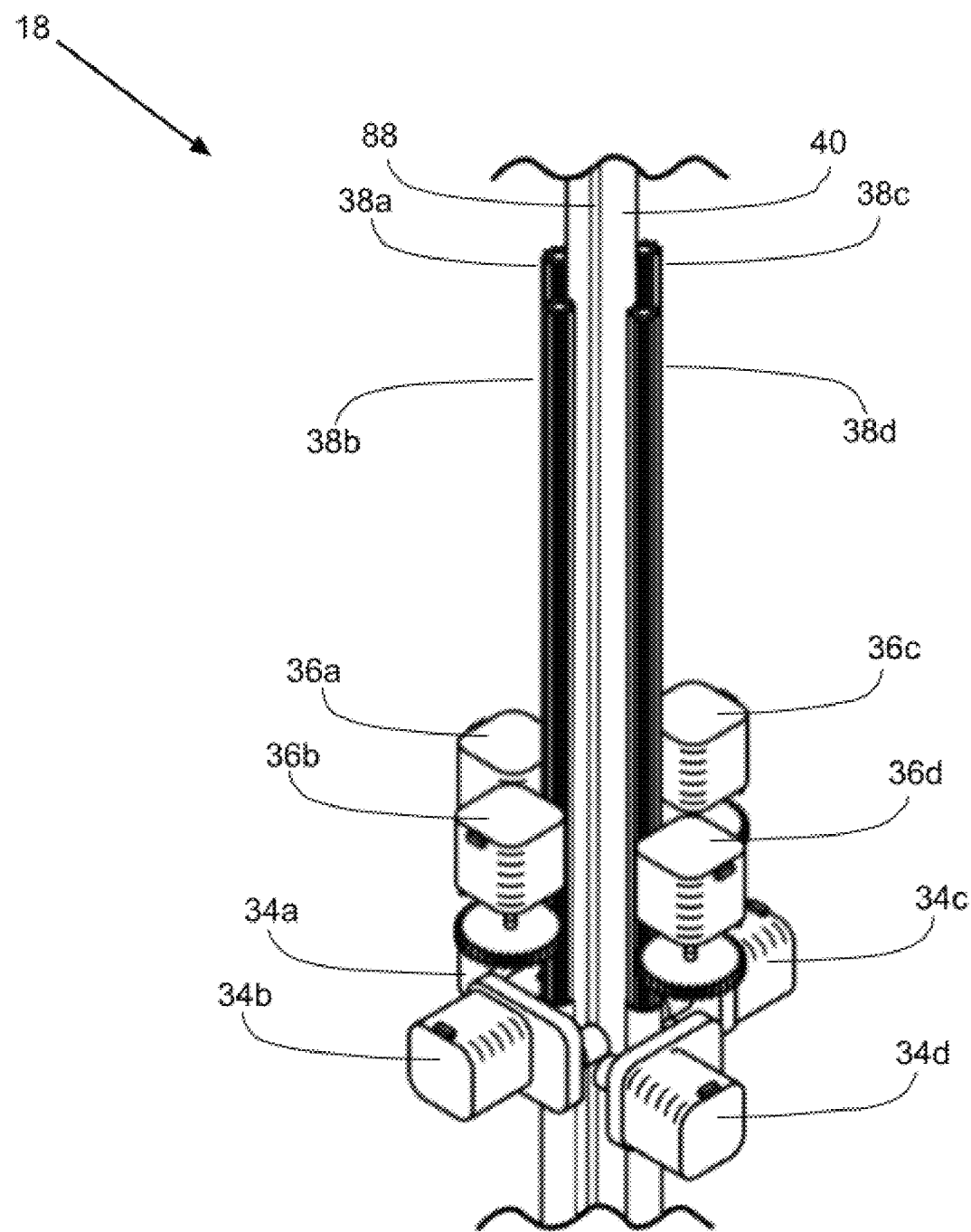
FIG. 7 shows an isometric view of the mid portion of the surgical device.
Figure 8:
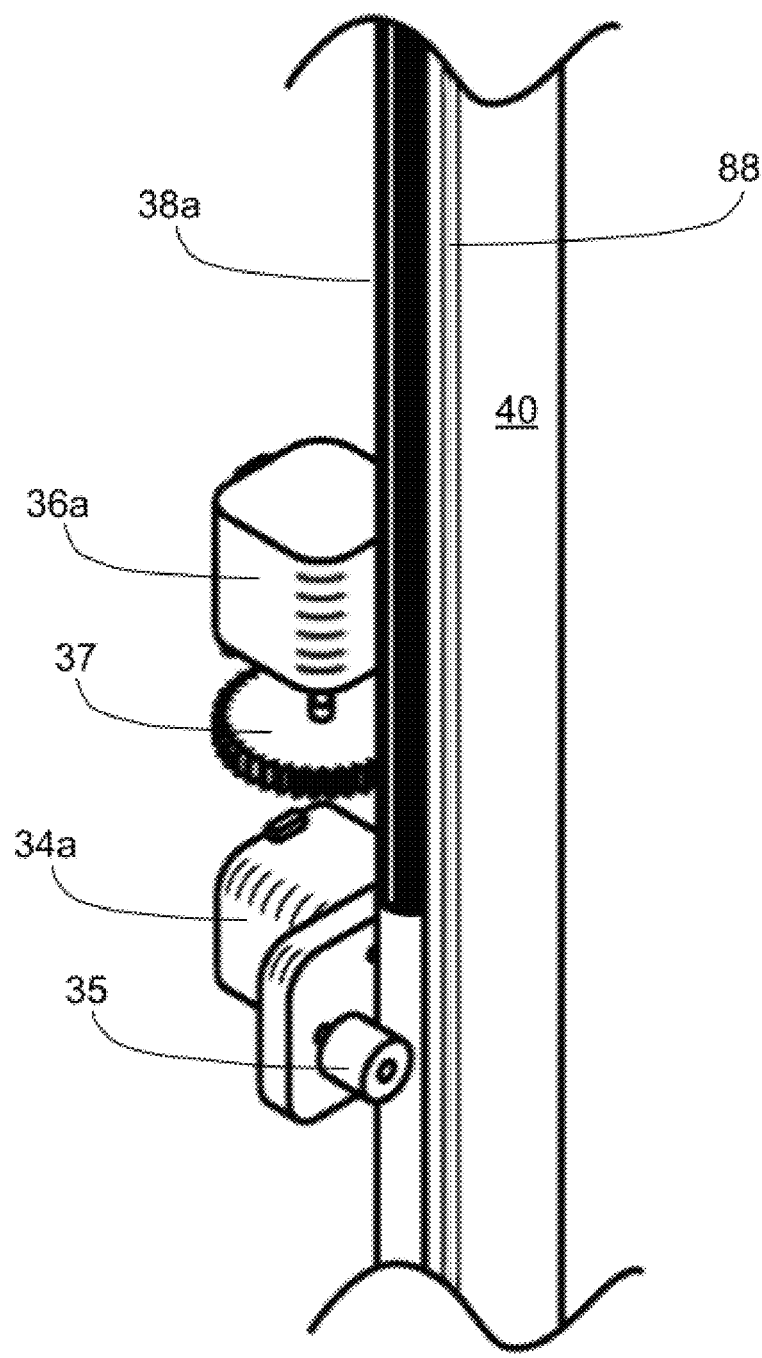
FIG. 8 shows an isometric view of the mid portion with all of the secondary arms removed save one to describe the mechanisms to raise, lower, or rotate a secondary arm.

Main shaft 40 and secondary shafts 38 are similar in that both are cylindrical in appearance and both use a friction wheel attached to a motor to raise and lower the shaft. However, different mechanisms are used to rotate the two shafts. To rotate main shaft 40 a gear having a key is mated with a keyway slot found along with longitudinal axis of main shaft 40 as shown in FIG. 3 and FIG. 4. Rotating the gear will in turn cause main shaft 40 to rotate. As for secondary shafts 38 the surface of the proximal half contains an arrangement of splines that interface with a gear. Rotating the gear will in turn cause secondary shafts 38 to rotate as shown in FIG. 7 and FIG. 8.

Main arm 32 and secondary arms 30 are similar in that both are comprised of two cylindrical segments that are hinged together. The proximal end of an arm is hinged to the distal end of a shaft and the distal end of an arm is attached to a tool. Secondary arms 30 differ from main arm 32 in a number of characteristics. The most significant difference is that surgical device 10 is capable of autonomously changing the tool attached to the distal end of main arm 32 while the tool attached to the distal end of secondary arms 30 must be manually changed. The process to autonomously replace the tool attached to the distal end of main arm 32 is described in FIG. 5. To manually change a tool on a secondary arm the associated shaft is raised so as to expose the tool. The surgeon, now having access to the tool is able to replace the tool with a desired tool. After the tool has been replaced the associated shaft is then lowered to reintroduce the arm back into abdominal cavity 14. Another difference is that main arm 32 is more complex than the secondary arms having more degrees of freedom and more powerful actuators and rotors. A final difference is that main arm 32 has a larger diameter than secondary arms 30 so as to accommodate more powerful motors, larger and sophisticated surgical tools, and to provide a larger port for the withdrawal of any dissected organ or tissue. Main arm 32 may have a diameter that ranges from 5 to 12 millimeters but preferably will have a diameter of about 10 millimeters. Secondary arms 30 may have a diameter that ranges from 3 to 5 millimeters but preferably will have a diameter of about 5 millimeters. The diameters of main arm 32 and secondary arms 30 will match the diameter of the shaft they are attached to.

Prior to surgery, the surgeon will make a determination of what tools will be needed for the surgery. Those tools that do not require the level of dexterity present in main arm 32 will be attached to the distal end of secondary arms 30. Those tools that require the level of dexterity present in main arm 32 will be positioned in grips 64 found in carousel 62 or attached to the distal end of main arm 32. Examples of tools that may be attached to the distal end of secondary arms 30 include but is not limited to lights, cameras, and graspers. Tools that may be attached to either main arm 32 or secondary arm 30 include but are not limited to dissectors, scissors, staplers, needle drivers, clip appliers, cauterizer, suction/irrigation tubes, and more.

Above introducer 22 and within mid portion 18 of surgical device 10 are motors and mechanisms that are used to provide longitudinal and rotational movement to secondary shafts 38 to which secondary arms 30 are attached to. Each shaft is manipulated by two motors. Motors 36 provides for the shaft to be rotated about its longitudinal axis and motors 34 provides for longitudinal movement of the shaft. To rotate a shaft, power is applied to a corresponding motor 36 that turns a gear. The gear engages matching splines found on the surface of the shafts thus causing the shaft to be rotated. To provide for longitudinal movement of a shaft, power is applied to corresponding motors 34 that turns a wheel. The wheel engages the surface of the shaft, which is smooth at this point, raising or lowering the shaft by the friction present between the surface of the wheel and shaft.

Upper portion 20 of surgical device 10 are motors and mechanisms that are used to provide longitudinal and rotational movement to main shaft 40 to which main arm 32 is attached to as well as motors and mechanisms to cause main tool 44 attached to the distal end of main arm 32 to be replaced by another tool that may be found in a inventory of tools held by carousel 62. Main shaft 40, to which main arm 32 is attached to, is manipulated by two motors. Motor 80 causes main shaft 40 to be rotated about its longitudinal axis and motor 70, not visible in FIG. 1, causes longitudinal movement of main shaft 40.

To rotate main shaft 40, power is applied to motor 80 to rotate gear 82 that engages matching gear 84 found on main shaft 40. As gear 84 must maintain its position relative to gear 82, gear 84 slides along main shaft 40 as it moves along its longitudinal axis by means of one or more key/keyway slots. To provide for longitudinal movement power may be applied to motor 70 so as to rotate wheel 72. As wheel 72 is rotated it frictionally engages the surface of main shaft 40 causing the shaft to move along its longitudinal axis. To replace main tool 44 with another tool, main shaft 40 is moved so that main tool 44 is opposite carousel 62. A motor within housing 66 will rotate carousel 62 so that an empty grip 64 is opposite main arm 32. Actuator 68 will then push housing 66 toward main tool 44 so that grip 64 may engage and cause to be removed from main arm 32 main tool 44. Actuator 68 will then retract housing 66 so that the motor within may rotate carousel 62 and position the grip containing the proper tool opposite main arm 32. Actuator 68 will then advance housing 66 so that grip 64 may engage and cause to be attached to main arm 32 desired main tool 44. Finally, actuator 68 will again retract housing 66 so that main shaft 40 may be moved along its longitudinal axis to deploy main arm 32 to the surgical site within abdominal cavity 14.

Thus far the mechanisms of surgical device 10 have been generally described and key components have been identified. The following paragraphs will provide greater details of the aforementioned mechanisms.

Figure 2B:
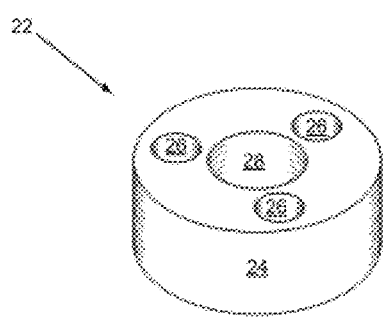
FIG. 2B shows isometric view of an alternate embodiment of the introducer containing a single larger opening for the main arm and three smaller openings for the secondary arms.
Figure 2C:
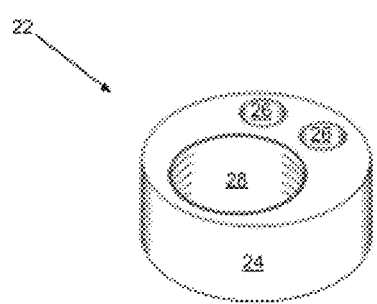
FIG. 2C shows an isometric view of an alternate embodiment of the introducer containing a single larger opening for the main arm and two smaller openings for the secondary arms.
Figure 2D:
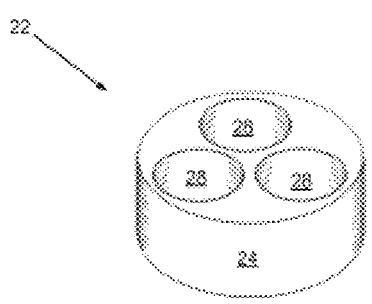
FIG. 2D shows an isometric view of an alternate embodiment of the introducer containing a three larger openings to accommodate three main arms.
Figure 2E:
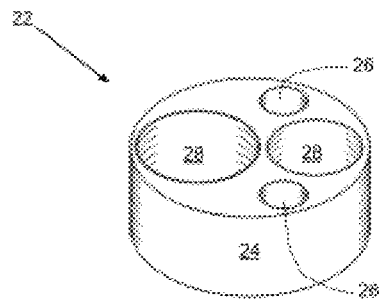
FIG. 2E shows an isometric view of an alternate embodiment of the introducer containing a two larger openings of varying diameter to accommodate two main arms and two smaller openings for secondary arms.

FIGS. 2A, B, C, D, and E shows varying embodiments of introducer 22. Introducer 22 serves as the interface between surgical device 10 and the patient that is undergoing surgery. Typically introducer 22 will be 20 to 25 millimeters in diameter, preferably 20 millimeters, and will be within a trocar that will be inserted through abdominal wall 12 via a surgeon made incision. The trocar will provide sealing functionality as well as ports for insufflation of abdominal cavity 14 by a gas, for secondary openings 26, and main openings 28. Secondary openings 26 will typically have a smaller diameter, in the range of 3 to 5 millimeters, and main openings 28 will typically have a larger diameter, in the range of 5 to 12 millimeters. Depending upon the type of surgical procedure to be conducted, fewer secondary arms 30 may be needed. FIG. 2A shows the preferred embodiment of introducer 22 with four secondary openings 26 and one main opening 28. FIG. 2B shows an alternate embodiment of introducer 22 with three secondary openings 26 and one main opening 28. FIG. 2C shows another alternate embodiment of introducer 22 with two secondary openings 26 and one main opening 28 that is larger than the main openings 28 of the introducer in FIG. 2A and FIG. 2B. FIG. 2D shows an introducer with three main openings 28 and no secondary openings 26. Finally, FIG. 2E shows an introducer with two main openings 28 of varying diameters and two secondary openings 26. The positioning of secondary openings 26 and main opening 28 may vary from what is shown to reduce the diameter of introducer 22 without departing from the spirit of the present invention. The diameters of the shafts and arms passing through their respective openings will be slightly less than the diameter of the opening itself.

FIG. 3 shows an isometric view of upper portion 20 of surgical device 10 where mechanisms to control carousel 62 and main shaft 40 are found. Carousel 62 serves as a placeholder for different tools that may be attached to the distal end of main arm 32. Carousel 62 is shown with four grips 64 to hold such tools and generally this is sufficient as it must be recalled that secondary arms 30 also have tools attached to them. Prior to surgery the surgeon will mount onto grips 64 those tools that will be needed for the surgery at hand. The surgeon may also replace a tool on a grip with another during surgery. Carousel 62 is shown in the figures with four grips but may accommodate additional grips beyond the four shown in the figures. Carousel 62 is mounted to housing 66 that contains within a motor to rotate carousel 62 about its central axis. Housing 66 may be moved along support arm 60 by actuator 68 so as to approach or retract from main shaft 40.

In addition to carousel 62 upper portion 20 also contains mechanisms to raise, lower, and rotate main arm 32. Motor 70 is used to provide vertical movement of main shaft 40 while motor 80 is used to rotate main shaft 40. To raise or lower main arm 40, power is applied to motor 70 so as to rotate wheel 72 which is frictionally engaged with main shaft 40. As wheel 72 is rotated clockwise, from the orientation of FIG. 3, the frictional engagement between wheel 72 and main shaft 40 will cause main shaft 40 to rise. As wheel 72 is rotated counterclockwise, from the orientation of FIG. 3, the frictional engagement between wheel 72 and main shaft 40 will cause main shaft 40 to lower. Wheel 74 freely rotates and is primarily used to promote the frictional forces between wheel 72 and main arm 40. Motor 80 is used to provide rotational movement of main shaft 40. To rotate main shaft 40 power is provided to motor 80 so as to rotate gear 82 which indirectly rotates main shaft 40 via gear 84 shown in the detail view of FIG. 4. Rotating gear 82 clockwise, from the orientation of FIG. 3, causes main shaft 40 to rotate counterclockwise. Conversely, rotating gear 82 counterclockwise causes main shaft 40 to rotate clockwise. As main shaft 40 moves vertically and motor 80 is stationary, gear 84 maintains its position adjacent to gear 82 because it interfaces with main shaft 40 with one or more key 86 in a corresponding keyway 88 as shown in FIG. 4. As main shaft 40 moves along its longitudinal axis, gear 84 will continue to engage stationary gear 82 by allowing main shaft 40 to slide through it while still engaging main shaft 40 for rotational purposes via the key 86 and keyway 88 interface.

Figure 5:
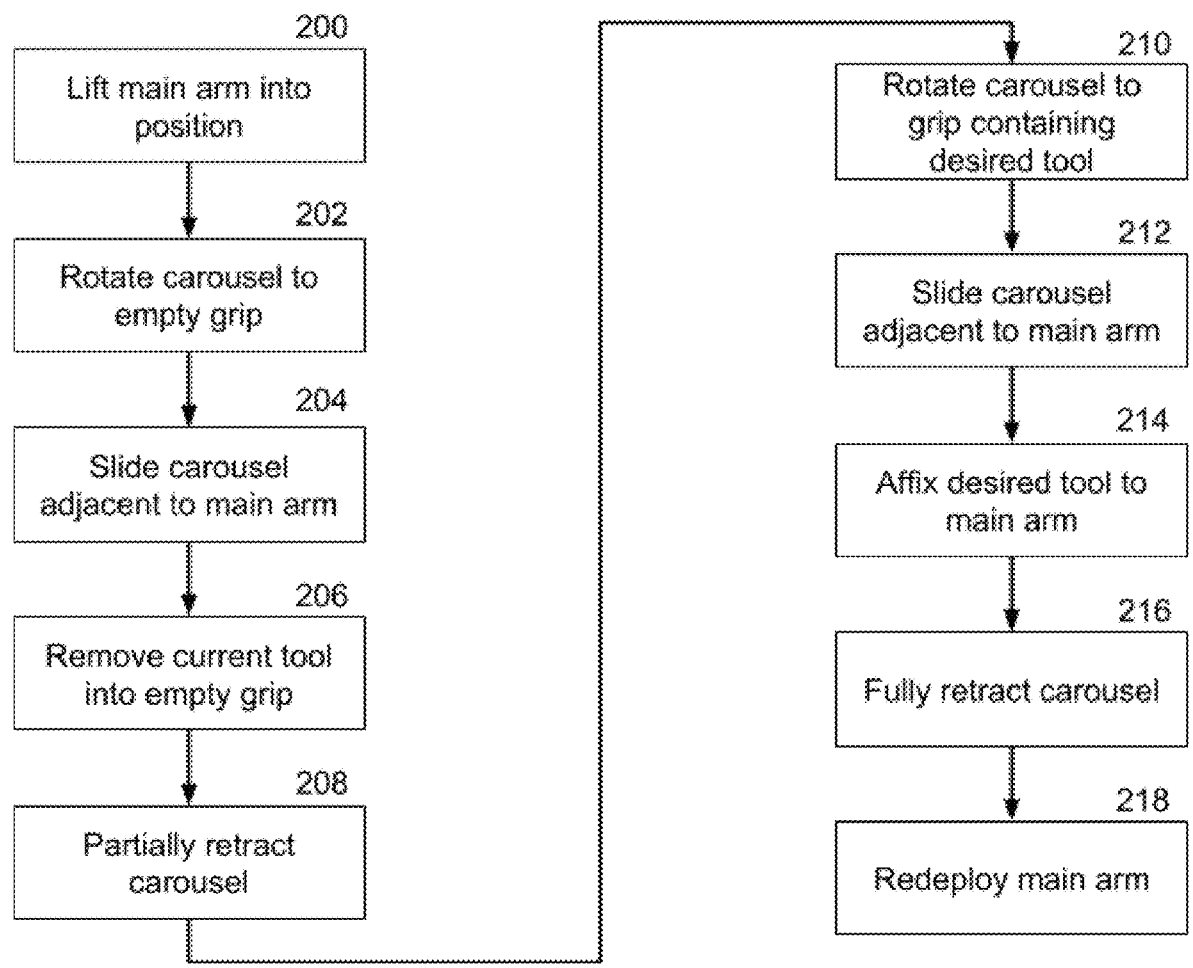
FIG. 5 shows a flowchart depicting the process to used by the surgical device to replace a tool on the main arm with a tool existing on the carousel.

FIG. 5 shows a flowchart that depicts how carousel 62 and main shaft 40 cooperate to change main tool 44 with another tool. During surgery, when carousel 62 is not performing any function, housing 66 it is attached to is positioned adjacent to actuator 68. Likewise, during surgery, main shaft is positioned so that main arm 32 is within the abdominal cavity to position main tool 44 at the surgical site. If the surgeon is required by the circumstances of the surgery to substitute main tool 44 with another the first step 200 will activate motor 70 and rotate wheel 72 in a clockwise direction as seen in FIG. 3 to raise main shaft 40. As main shaft 40 is being raised main arm 32 will be straightened so as to move through opening 28 in introducer 22. Motor 70 will continue to raise main shaft 40 until main arm 32 is opposite carousel 62. Next, or concurrently with step 200, the motor within housing 66 will rotate carousel 62 so that an empty grip 64 is facing main shaft 40 as shown in step 202. Once main tool 44 is opposite carousel 62, actuator 68 moves housing 66 along support arm 60 towards main tool 44, step 204, so that grip 64 is able to engage main tool 44 and remove it, step 206. After main tool 44 has been removed, actuator 68 will retract housing 66 so the carousel may be freely rotated by motor within housing 66 as shown in step 208. At this point, motor within housing 66 will rotate carousel 62 so that the grip containing the desired tool is opposite main arm 32 as depicted in step 210. Now actuator 68 will again move housing 66 towards main arm 32, step 212, and attach the desired tool to main arm 32, step 214. Once the desired tool has been attached to main arm 32 actuator 68 will fully retract housing 66 so that it is adjacent to actuator 68, step 216. Concurrently with step 216 or independent thereof, motor 70 will activate and rotate wheel 72 in a counterclockwise direction as seen in FIG. 3 to lower main shaft 40 and thus lowering main arm 32 through opening 28 in introducer 22 until main tool 44 is positioned at the surgical site.

Figure 6:
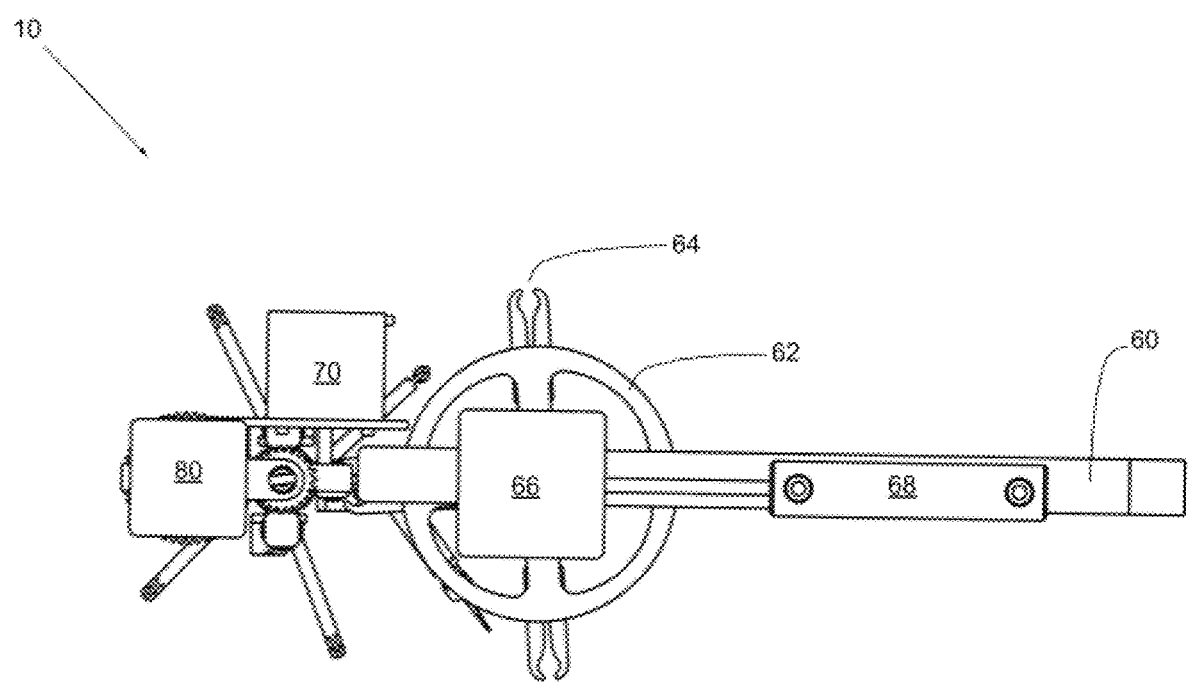
FIG. 6 shows a top view of the surgical device.

FIG. 6 shows a top view of surgical device 10 so as to provide the reader with another view. Visible is support arm 60 which is used to guide housing 66 along its longitudinal axis and as a mount for actuator 68. Housing 66 contains within a motor which is used to rotate carousel 62. Also clearly visible from the top view is motor 70 which is used to raise or lower main shaft 40 and motor 80 which is used to rotate main shaft 40.

FIG. 7 shows an isometric view of mid portion 18 of surgical device 10 where mechanisms to control secondary shafts 38 are found. Each secondary shaft 38 is attached to a secondary arm 30 to rotate secondary arm 30 or to raise or lower it. FIG. 7 shows four secondary shafts 38; thus this particular embodiment would utilize introducer 22 shown in FIG. 2A. If introducer 22 shown in FIG. 2B were to be utilized then only three secondary shafts 38 would be present equally interspaced about main shaft 40. If introducer 22 shown in FIG. 2C were to be utilized then only two secondary shafts 38 would be present aside main shaft 40. This same logic proceeds to the remaining introducers shown in FIG. 2D and FIG. 2E. Each secondary shaft 38 makes use of the same motorized means to rotate or to vertically translate the shaft. Also visible in FIG. 7 is main shaft 40 and keyway 88 that allows main shaft 40 to move through gear 84. Keyway 88 is engaged by key 86 found on gear 84 so that main shaft 40 may be rotated by a force acting on gear 84.

FIG. 8 shows an isometric view of mid portion 18 showing only one secondary shaft 38 and its associated mechanisms so as to simplify the disclosure of how the secondary shafts 38 rotate about or vertically translate along its longitudinal axis. Each secondary shaft 38 is comprised of two distinct sections; a lower section that contains a smooth surface and an upper section that contains a surface consisting of splines. To rotate secondary shaft 38a power is applied to motor 36a to turn gear 37 that is engaged with the spline section of secondary shaft 38a. By turning gear 37, motor 36a can control the direction, clockwise or counter clockwise; speed of rotation; and the amount of rotation to be performed by secondary shaft 38a. Motor 36a is attached to a framework about surgical device 10 which is not shown and is not part of the disclosure. To vertically translate secondary shaft 38a along its longitudinal axis power is applied to motor 34a in order to turn wheel 35 that is frictionally engaged with the smooth section of secondary shaft 38a. By turning wheel 35, motor 34a can control the direction, up or down, and speed of the vertical translation as well as the amount of vertical translation. Opposite of wheel 35 is another wheel, not visible, that is unpowered and provides a counter force to the force applied against secondary shaft 38a by wheel 35 to ensure the proper level of frictional engagement by wheel 35 against secondary shaft 38a. Motor 34a is attached to a framework about surgical device 10 which is not shown and is not part of the disclosure. The means to rotate or vertically translate secondary shaft 38a described here is also utilized to rotate or vertically translate the other remaining secondary shafts.

Figure 9:
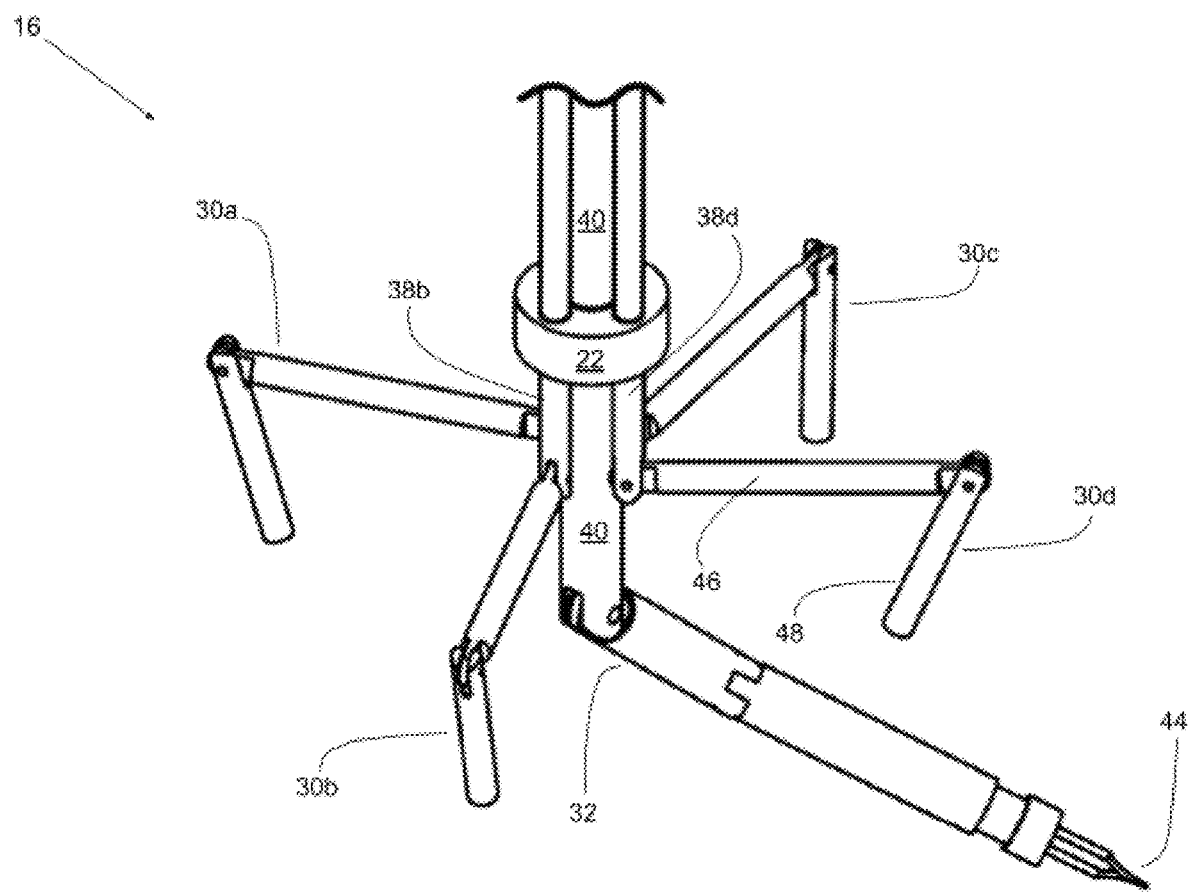
FIG. 9 shows an isometric view of the lower portion of the surgical device.

FIG. 9 shows an isometric view of lower portion 16 with introducer 22 demarcating the position of abdominal wall 12 which is not shown but exists in the same plane as introducer 22. Those parts of surgical device 10 present below introducer 22 are in abdominal cavity 14 while those parts above introducer 22 are outside of the abdominal cavity 14. FIG. 9 shows the preferred embodiment of surgical device 10 with introducer 22 identified in FIG. 2A that provides for five openings: four openings for secondary shafts 38 and one opening for main shaft 40. Preferably main shaft 40 will range from 5 to 12 millimeters in diameter while secondary shafts 38 will range from 3 to 5 millimeters in diameter. The diameters of main arm 32 and secondary arms 30 will match the diameter of the shaft they are attached to. Other embodiments utilize introducer 22 shown in FIG. 2B through 2E that support, a variety of configurations of main shafts 40 and secondary shafts 38. Secondary shafts 38 may be rotated or translated vertically by mechanisms described in FIG. 7 and FIG. 8.

Figure 10:
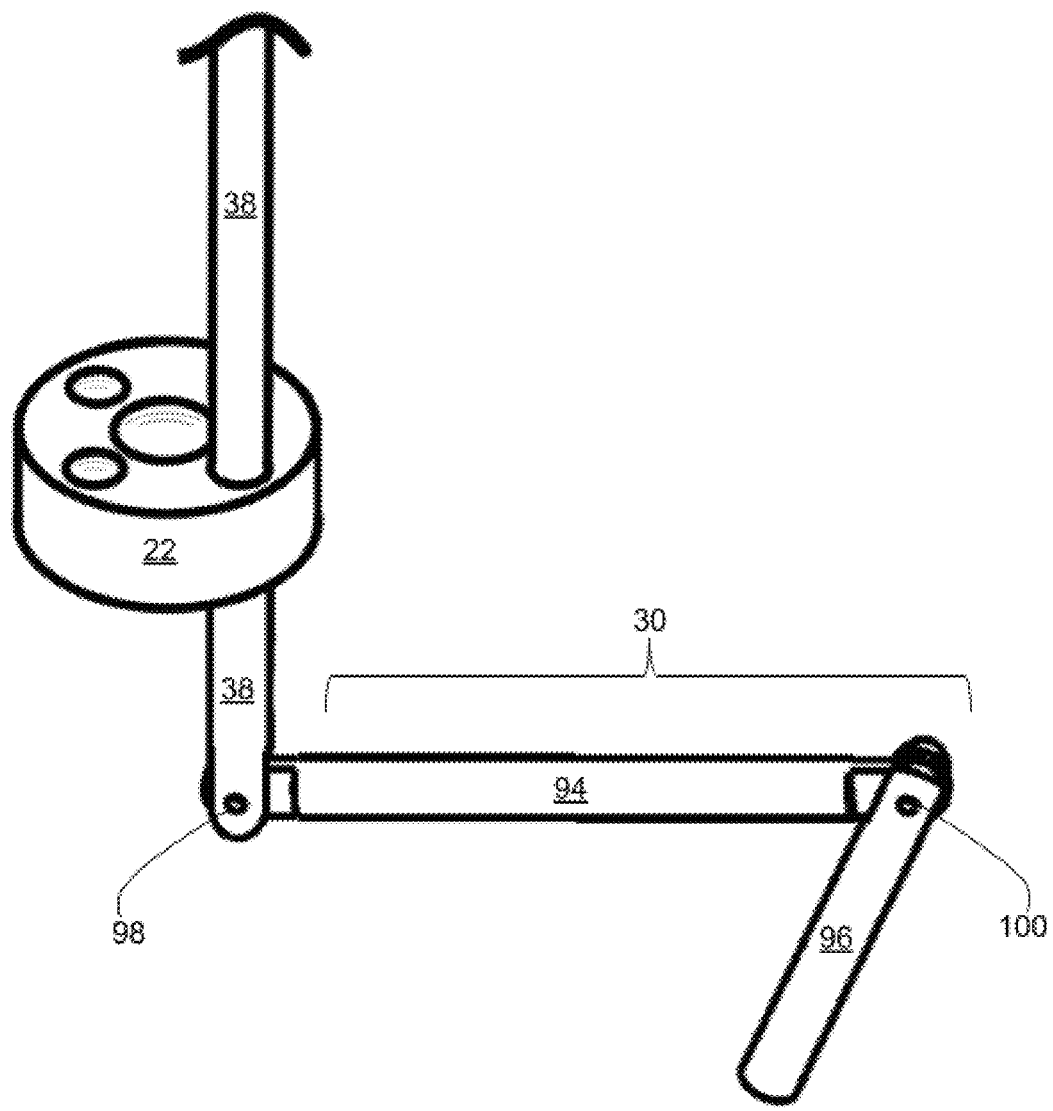
FIG. 10 shows an isometric view of a single secondary arm passing through an introducer.
Figure 11:
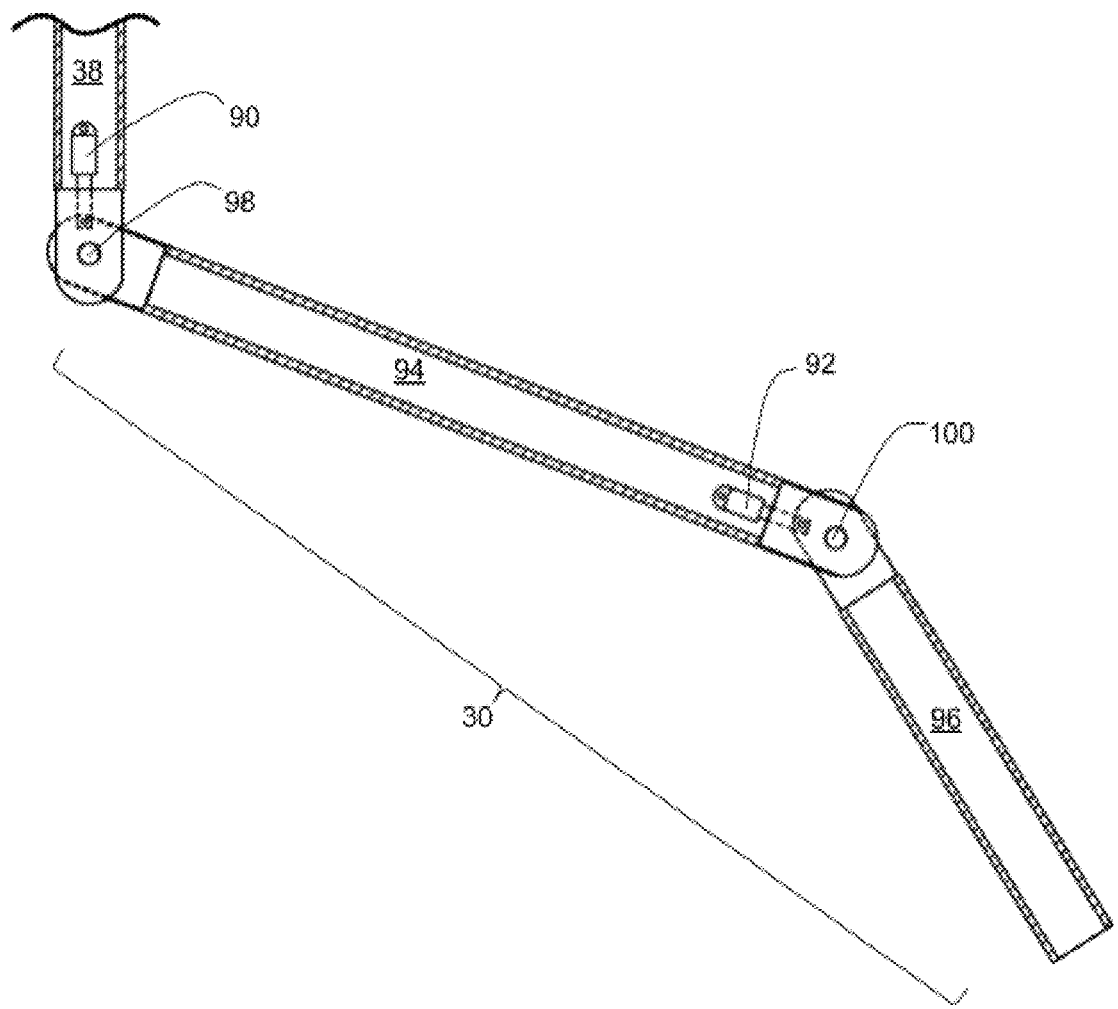
FIG. 11 shows a cutaway view of a secondary arm in order to display the mechanisms that manipulate the arm.

FIG. 10 shows an isometric view of lower portion 16 displaying only one secondary shaft 38 and its associated arm 30 along with introducer 22 demarcating the position of abdominal wall 12 which is not shown but exists in the same plane as introducer 22 so as to better disclose the visible portions of a secondary arm and its associated shaft. The discussion here also applies to the remaining secondary shafts and their associated arms. Shown is distal portion of secondary shaft 38 extending through introducer 22 and connecting to secondary arm 30 via hinge joint 98. Secondary arm 30 is comprised of two segments: proximal segment 94 and distal segment 96 which are connected by hinge joint 100. A tool, not shown, is attached to distal segment 96 opposite hinge joint 100. Mechanisms to manipulate proximal segment 94 and distal segment 96 are shown in FIG. 11 and are comprised of two actuators. A first actuator, actuator 90, is a linear actuator with one end pivotality joined to secondary shaft 38 and the opposing end pivotality joined to proximal segment 94. Upon receiving an electrical signal from the controlling computer, actuator 90 may increase or decrease its overall length thus causing proximal segment 94 to rotate about hinge joint 98. A second actuator, actuator 92, is also a linear actuator with one end pivotality joined to proximal segment 94 and the opposing end pivotality joined to distal segment 96. Upon receiving an electrical signal from the controlling computer, actuator 92 may increase or decrease its overall length thus causing distal segment 96 to rotate about hinge joint 100.

Figure 12:
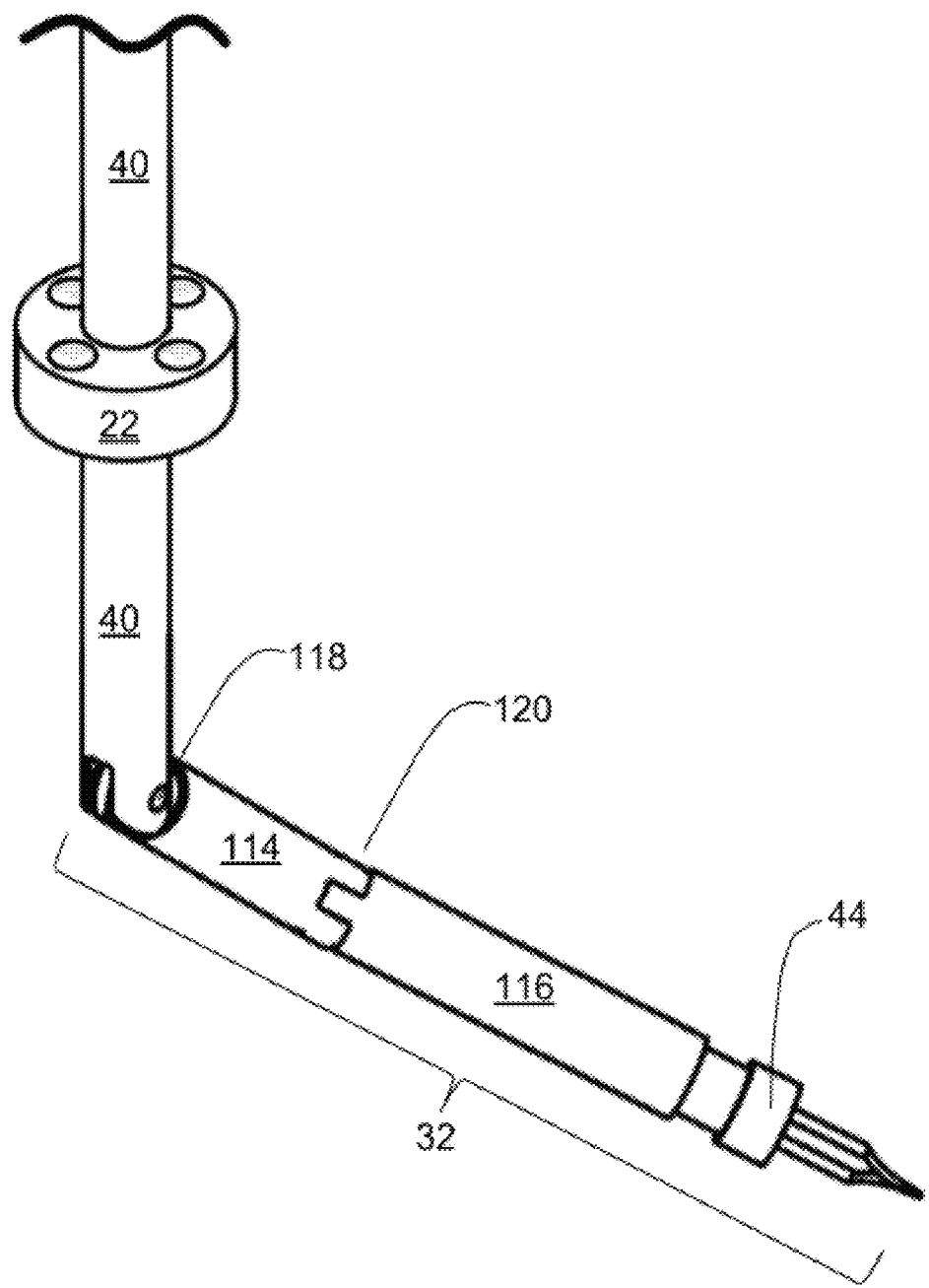
FIG. 12 shows an isometric view of the main arm passing through an introducer.
Figure 13:
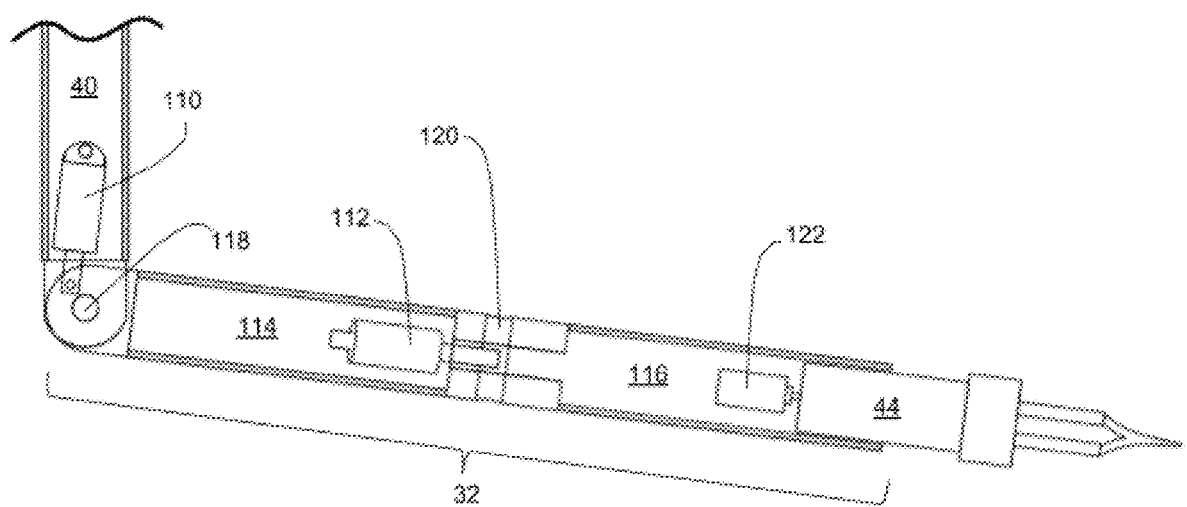
FIG. 13 shows a cutaway view of a main arm in order to display the mechanisms that manipulate the arm.

FIG. 12 shows an isometric view of lower portion 16 displaying only main shaft 40 and main arm 32 along with introducer 22 demarcating the position of abdominal wall 12 which is not shown but exists in the same plane as introducer 22 so as to better disclose the visible portions of main arm 32 and main shaft 40. Shown is distal portion of main shaft 40 extending through introducer 22 and connecting to main arm 32 via hinge joint 118. Main arm 32 is comprised of two segments: proximal segment 114 and distal segment 116 which are connected by hinge joint 120. Main tool 44 is attached to distal segment 116 opposite hinge joint 120. Mechanisms to manipulate proximal segment 114 and distal segment 116 are shown in FIG. 13 and are comprised of two actuators and a rotor. A first actuator, actuator 110, is a linear actuator with one end pivotality joined to main shaft 40 and the opposing end pivotality joined to proximal segment 114. Upon receiving an electrical signal from the controlling computer, actuator 110 may increase or decrease its overall length thus causing proximal segment 114 to rotate about hinge joint 118. A second actuator, actuator 112, is also a linear actuator with one end pivotality joined to proximal segment 114 and the opposing end pivotality joined to distal segment 116. Upon receiving an electrical signal from the controlling computer, actuator 112 may increase or decrease its overall length thus causing distal segment 116 to rotate about hinge joint 120. An additional degree of freedom is provided to main arm 32 by rotor 122 so that main tool 44 may be rotated clockwise or counter-clockwise.

Figure 14:
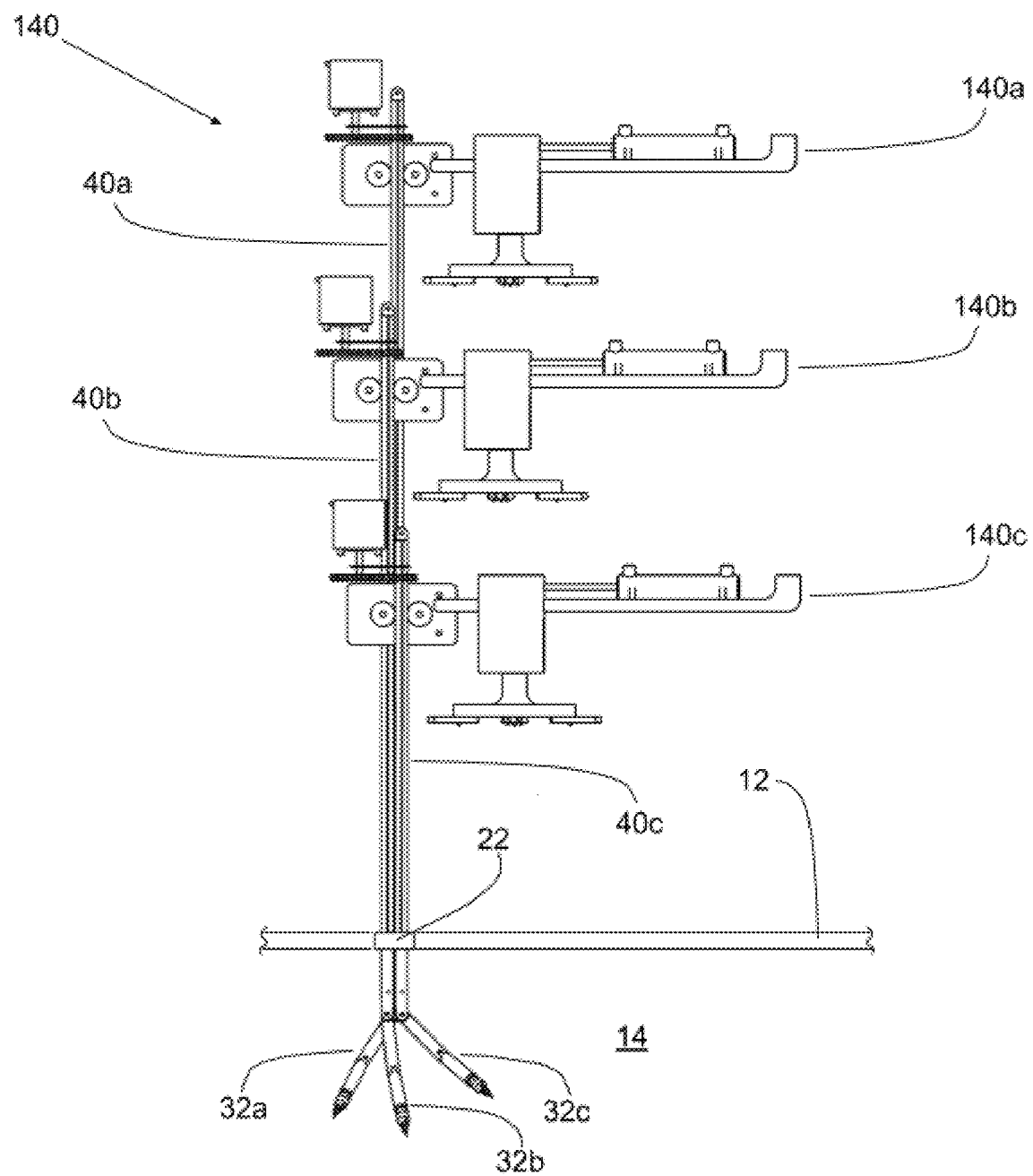
FIG. 14 shows an embodiment containing a combination of the surgical device of the present invention.

The surgical device of the present invention may be used in aggregate if the surgeon determines that the surgery would be more appropriately performed using only the more capable main arms without any secondary arms. In such a scenario secondary shafts 38 would be removed from each surgical device 10 to be aggregated leaving only main shaft 40. By increasing the length of main shaft 40, upper portion 20 of each surgical device may operate to rotate and vertically translate main shaft 40 as well as change the surgical tool at the distal end of main arm 32 without interfering with the operations of the remaining surgical devices 10. This arrangement is shown in FIG. 14 where secondary embodiment 140 of surgical device 10 where an aggregate of three surgical devices, 140a, 140b, and 140c, each having corresponding main shafts 40a, 40b, and 40c along with main arms 32a, 32b, and 32c, are combined with the introducer 22 shown in FIG. 2D. Although the surgeon would have fewer arms to work with, using the main arms does provide additional capabilities to the surgeon such as stronger motors and actuators, additional degrees of freedom, and the ability to autonomously replace the surgical tool at the distal end of each arm.

Figure 15:
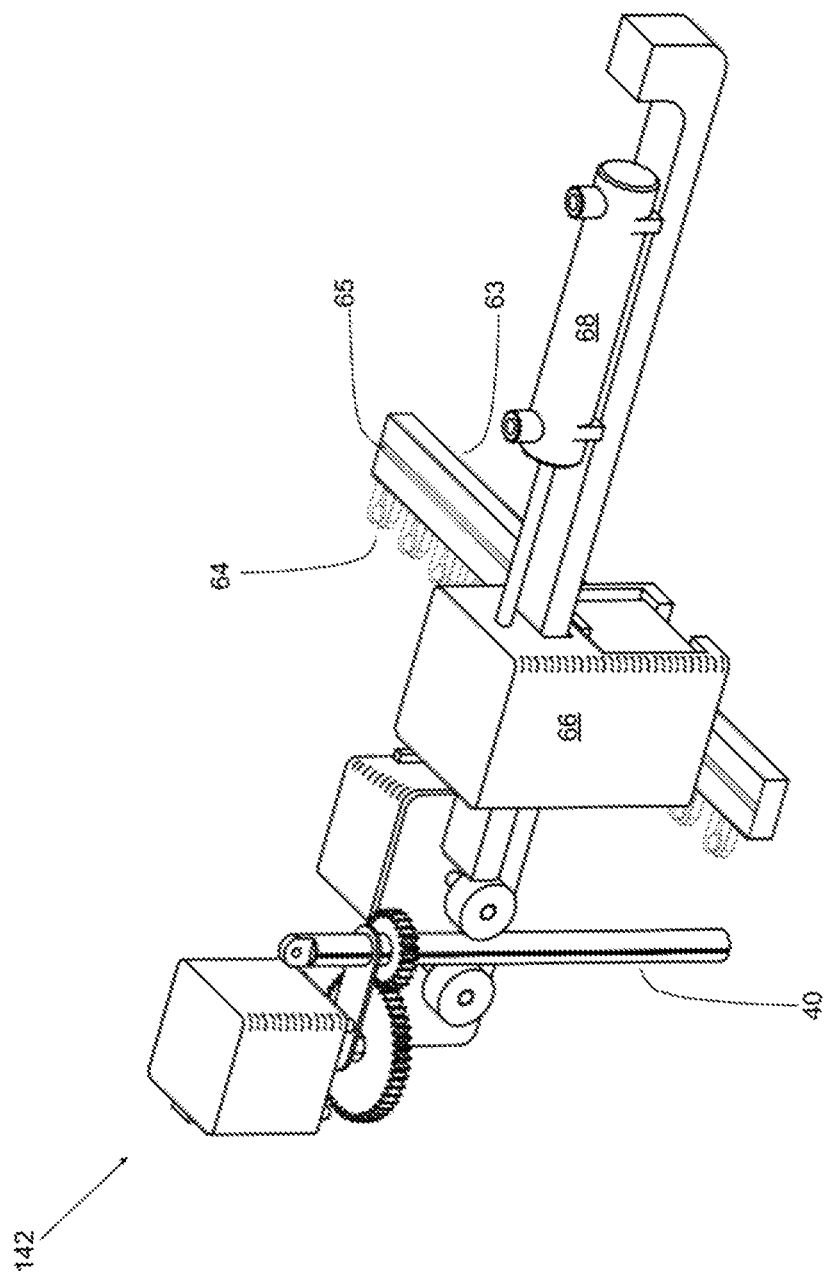
FIG. 15 shows an alternate embodiment of the surgical device of the present invention.

FIG. 15 shows alternate embodiment 142 of the surgical device of the present invention. Here upper portion 20 of surgical device 142 differs from the preferred embodiment of surgical device 10 in that carousel 62 is replaced by rail 63 that supports along one side multiple grips 64. The motor within housing 66 turns a gear that engages track 65 and enables rail 63 to move laterally along track 65. If the surgeon is required by the circumstances of the surgery to substitute main tool 44 with another, the same method as depicted in FIG. 5 is basically followed except that now rail 63 is moved towards or away from main shaft by actuator 68 while the motor within housing 66 moves rail 63 laterally to position the desired grip 64 opposite main shaft 40.

Figure 16:
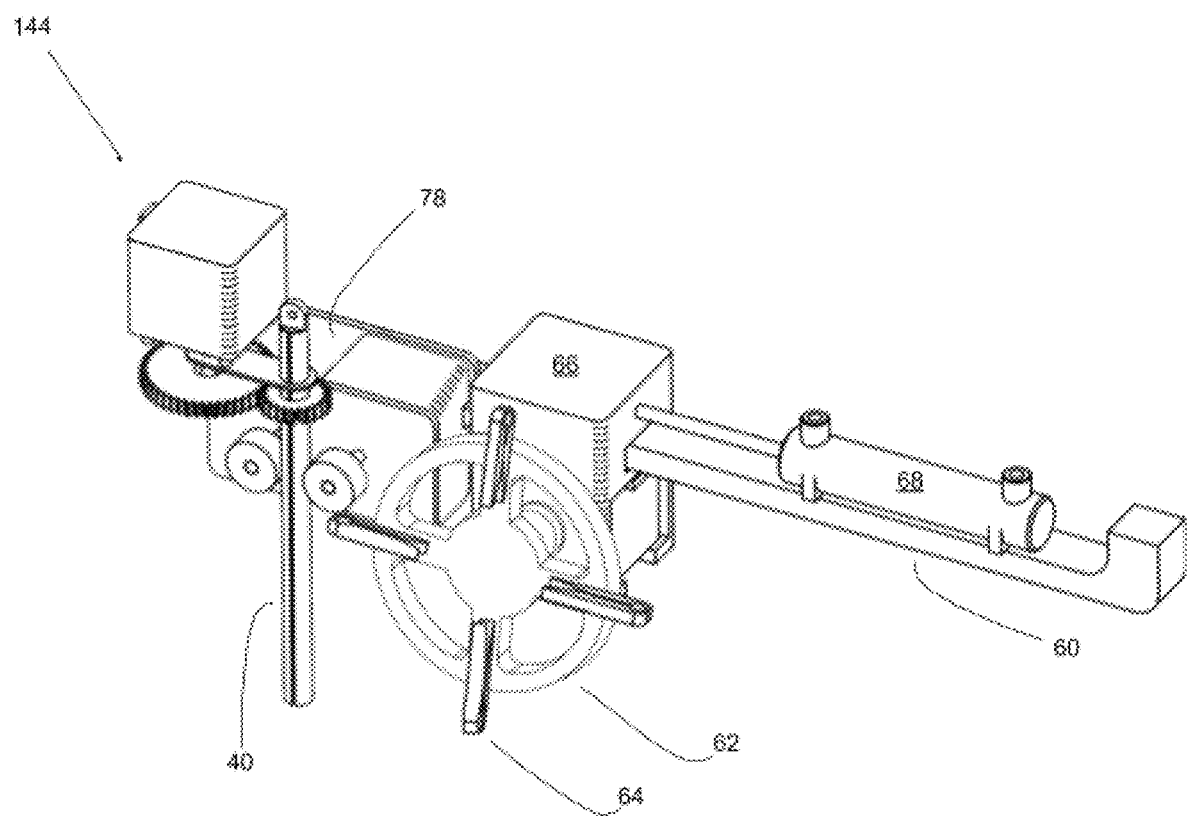
FIG. 16 shows an alternate embodiment of the surgical device of the present invention.

FIG. 16 shows alternate embodiment 144 of the surgical device of the present invention. Here upper portion 20 of surgical device 144 differs from the preferred embodiment of surgical device 10 in that carousel 62 and motor 66 are mounted perpendicularly onto support arm 60 as compared to surgical device 10. Actuator 68 still functions to move motor 66 along support arm 60 while motor in housing 66 rotates carousel 62 so that grip 64 may be positioned opposite main shaft 40. To align main shaft 40 with grip 64 a horizontal offset must be applied to support arm 60. Rather than attaching support arm 60 to plate 76 as is shown in FIG. 3, in this embodiment support arm 60 will be attached to rear plate 78. If the surgeon is required by the circumstances of the surgery to substitute main tool 44 with another, the same method as depicted in FIG. 5 is followed.

Figure 17:
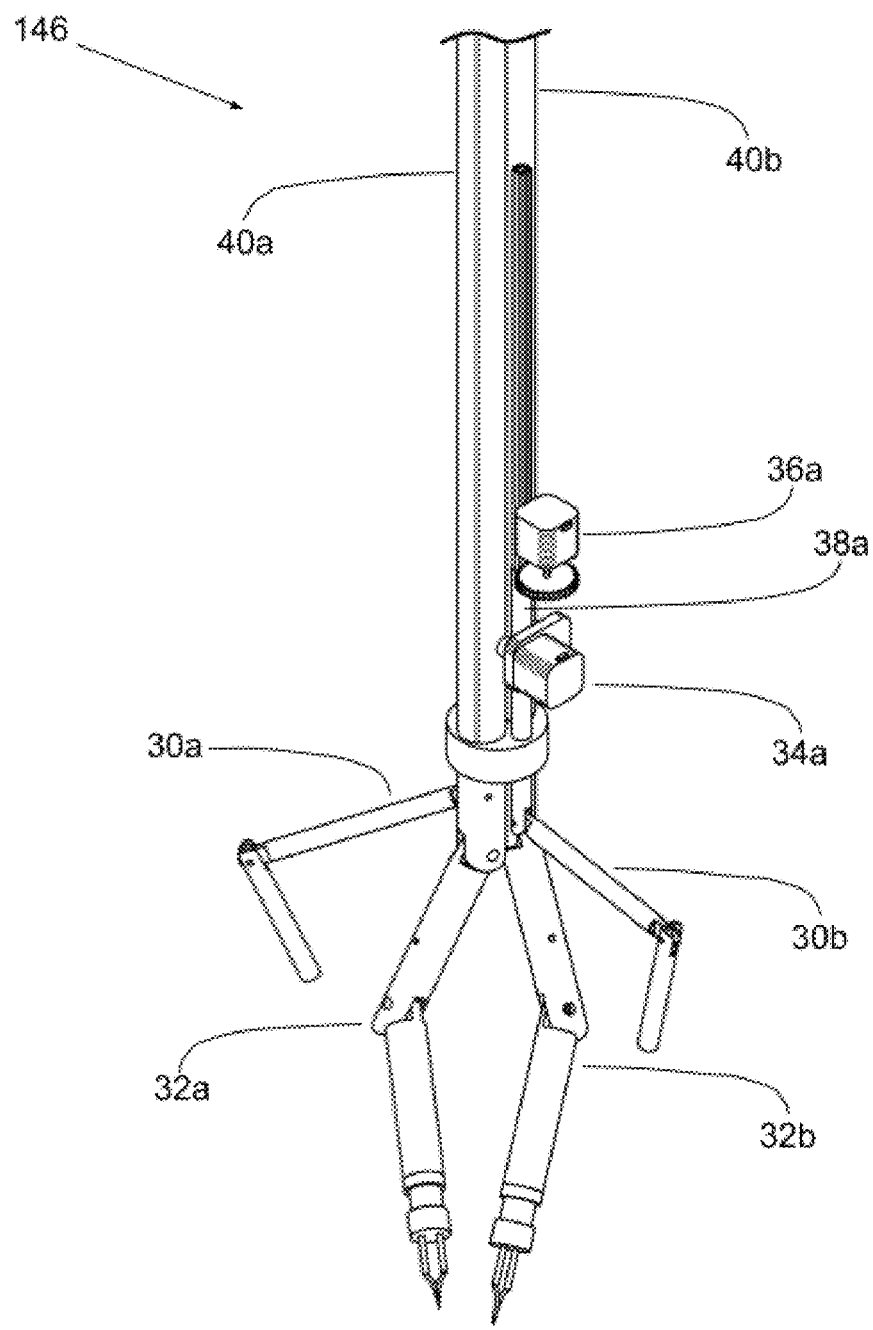
FIG. 17 shows an alternate embodiment of the surgical device of the present invention.

FIG. 17 shows alternate embodiment 146 of the surgical device of the present invention were multiple main arms 32 and secondary arms 30 are used along with introducer 22 shown in FIG. 2E. Secondary arm 30b and corresponding motors 36b and 38b are not visible as they are behind main shafts 40a and 40b. In this embodiment secondary arm 30a may host a camera while secondary arm 30b may host a light as these surgical tools do not require much precision while main arms 40*a* and 40*b* may support surgical tools that require greater precision during use.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above.

What is claimed is:

1. A surgical device comprising:
    a main shaft being cylindrical and having proximal and distal ends and having a keyway slot along its longitudinal axis;
    a main arm having proximal and distal ends where the proximal end of main arm is attached to distal end of main shaft and a surgical tool being releasably attached to the distal end of main arm;
    a motor driving a friction wheel that operably engages the surface of the main shaft such that rotational motion by the friction wheel causes the main shaft to translate vertically;
    a motor driving a first gear that engages a second gear about the main shaft the second gear engaging the main shaft by means of a key within the keyway slot so that rotation of the second gear causes the main shaft to rotate about its longitudinal axis while allowing the main shaft to vertically translate through the second gear; and
    an introducer fitted to an incision having openings to allow the main shaft to pass therethrough so that the surgical tool attached to the main arm may be deployed at a surgical site.

2. The surgical device of claim 1 further comprising a mechanism to store a plurality of surgical tools the mechanism comprising:
    a horizontal support arm having first and second ends with first end attached to the surgical device;
    a housing containing a motor that rotates a carousel the carousel having a plurality of grips where each grip holds a surgical tool the housing transversing the length of the support arm; and
    an actuator mounted to second end of the support arm and engaging the housing so as to cause the housing to transverse along the length of the support arm.

3. The surgical device of claim 2 further comprising a method of replacing the surgical tool found at the distal end of main arm with a surgical tool found in a grip the method comprising the steps of:
    lifting the main arm to a height such that the surgical tool attached to distal end of the main arm may be engaged by a grip;
    rotating the carousel so that an empty grip is opposite the surgical tool attached to distal end of the main arm;
    moving the carousel towards the main shaft so that empty grip engages and retrieves the surgical tool attached to distal end of the main arm;
    retracting the carousel from the main arm;
    rotating the carousel so that the grip containing the desired surgical tool is opposite distal end of main arm;
    moving the carousel towards the main shaft so that the grip containing the desired surgical tool engages and attaches the surgical tool to distal end of the main arm;
    retracting the carousel from the main arm; and
    lowering the main arm so that the surgical tool attached to distal end of the main arm is deployed.

4. The surgical device of claim 1 wherein the diameter of the main shaft is larger than the diameter of any secondary shaft.

5. The surgical device of claim 1 further comprising a mechanism to store a plurality of surgical tools the mechanism comprising:
    a horizontal support arm having first and second ends with first end attached to the surgical device;
    a housing containing a motor that linearly translates a rail mounted perpendicularly to the support arm having a plurality of grips where each grip holds a surgical tool the housing transversing the length of the support arm; and
    an actuator mounted to second end of the support arm and engaging the housing so as to cause the housing to transverse along the length of the support arm.

6. The surgical device of claim 5 further comprising a method of replacing the surgical tool found at the distal end of main arm with a surgical tool found in a grip the method comprising the steps of:
    lifting the main arm to a height such that the surgical tool attached to distal end of the main arm may be engaged by a grip;
    translating the rail so that an empty grip is opposite the surgical tool attached to distal end of the main arm;
    moving the rail towards the main shaft so that empty grip engages and retrieves the surgical tool attached to distal end of the main arm;
    retracting the rail from the main arm;
    translating the rail so that the grip containing the desired surgical tool is opposite distal end of main arm;
    moving the rail towards the main shaft so that the grip containing the desired surgical tool engages and attaches the surgical tool to distal end of the main arm;
    retracting the rail from the main arm; and
    lowering the main arm so that the surgical tool attached to distal end of the main arm is deployed.

7. The surgical device of claim 1 further comprising one or more secondary shafts where the secondary shafts are cylindrical, adjacent and parallel to the main shaft, and having proximal and distal ends where the surface of the proximal portion of the secondary shaft contains an arrangement of vertical splines
    the secondary shafts each comprising:
        a secondary arm with proximal and distal ends where the proximal end of the secondary arm is attached to distal end of the secondary shaft and a surgical tool being releasably attached to the distal end of the secondary arm;
        a motor driving a friction wheel that operably engages the surface of distal portion the secondary shaft such that rotational motion by the friction wheel causes the secondary shaft to translate vertically; and
        a motor driving a gear that engages the arrangement of vertical splines such that when the gear is rotated by the motor the secondary shaft will rotate in the opposite direction;
    the introducer having openings for the one or more secondary shafts to pass therethrough so that the surgical tools attached to the secondary arms may be deployed at a surgical site.

8. A surgical device comprising:
a plurality of main shafts each main shaft
- being cylindrical;
- having proximal and distal ends;
- having a keyway slot along its longitudinal axis;
- having a motor driving a friction wheel that operably engages the surface of the main shaft such that rotational motion by the friction wheel causes the main shaft to translate vertically;
- having a motor driving a first gear that engages a second gear about the main shaft the second gear engaging the main shaft by means of a key within the keyway slot so that rotation of the second gear causes the main shaft to rotate about its longitudinal axis while allowing the main shaft to vertically translate through the second gear;
- having a main arm with proximal and distal ends where the proximal end of the main arm is attached to distal end of the main shaft and a surgical tool being releasably attached to the distal end of the main arm;
- having a mechanism to store a plurality of surgical tools the mechanism comprising:
  - a horizontal support arm having first and second ends with first end attached to the surgical device;
  - a housing containing a motor that rotates a carousel the carousel having a plurality of grips where each grip holds a surgical tool the housing transversing the length of the support arm; and
  - an actuator mounted to second end of the support arm and engaging the housing so as to cause the housing to transverse along the length of the support arm;

an introducer fitted to an incision having openings to allow the main shafts to pass therethrough so that the surgical tool attached to the main arms may be deployed at a surgical site.

* * * * *